US012678505B2

(12) United States Patent
Kotani et al.

(10) Patent No.: US 12,678,505 B2
(45) Date of Patent: Jul. 14, 2026

(54) LEAKAGE INHIBITING AGENT FOR LOCAL INJECTION PREPARATION, LOCAL INJECTION PREPARATION INCLUDING THE SAME, AND METHOD FOR PRODUCING LOCAL INJECTION PREPARATION

(71) Applicant: NITTA GELATIN INC., Osaka (JP)

(72) Inventors: Kazuki Kotani, Yao (JP); Yosuke Hiraoka, Yao (JP)

(73) Assignee: NITTA GELATIN INC., Osaka (JP)

( * ) Notice: Subject to any disclaimer, the term of this patent is extended or adjusted under 35 U.S.C. 154(b) by 358 days.

(21) Appl. No.: 18/291,846

(22) PCT Filed: Aug. 31, 2022

(86) PCT No.: PCT/JP2022/032793
§ 371 (c)(1),
(2) Date: Jan. 24, 2024

(87) PCT Pub. No.: WO2023/089906
PCT Pub. Date: May 25, 2023

(65) Prior Publication Data
US 2024/0342289 A1       Oct. 17, 2024

(30) Foreign Application Priority Data

Nov. 16, 2021    (JP) ................................. 2021-186121

(51) Int. Cl.
*A61K 47/42*          (2017.01)
*A61K 9/00*           (2006.01)
*A61K 9/08*           (2006.01)
(52) U.S. Cl.
CPC ............ *A61K 47/42* (2013.01); *A61K 9/0019* (2013.01); *A61K 9/08* (2013.01)
(58) Field of Classification Search
CPC .................................. A61K 47/42; A61K 9/08
See application file for complete search history.

(56) References Cited

U.S. PATENT DOCUMENTS

| | | |
|---|---|---|
| 6,319,260 B1 | 11/2001 | Yamamoto |
| 2003/0105061 A1 | 6/2003 | Ishikawa et al. |
| 2006/0269987 A1 | 11/2006 | Dolphin et al. |
| 2020/0030386 A1 | 1/2020 | Petito |

FOREIGN PATENT DOCUMENTS

| | | |
|---|---|---|
| JP | 56-68607 A | 6/1981 |
| JP | 2001-192336 A | 7/2001 |
| JP | 2007-001989 A | 1/2007 |
| JP | 2008-541743 A | 11/2008 |

OTHER PUBLICATIONS

Hiroyuki Bando et al., "Endoscopic Mucosal resection of colon by injection of gelatin solution", Endoscopic Forum for digestive disease, 1994, vol. 10, No. 2, pp. 193-196, ISSN 0912-0505 Abstract, p. 193 Right-column Lines 11-17, p. 194 Left-column Lines 1-5, p. 194 Right-column Lines 13-14, p. 195 Left-column Line 32-Right-column Line 6.

Hermel, H., et al., "A New Consideration of the Molecular Mass-Viscosity Correlation of Gelatin", The Journal of Photographic Science, 1993, vol. 41, pp. 9-10.

Yoshida, T., et al., "Viscosity: An important factor in predicting the performance of submucosal injection materials", Materials and Design, 2020, vol. 195, No. 109008, pp. 1-11.

Sakurai, Toshihiro et al. "Endoscopic demucosation by the gelatine aqueous solution injection method" Clinical Gastroenterology, 1993, vol. 8, No. 13, pp. 2147-2152.

Takashi Ohno et al, Determination of Molecular Weight Distribution of Gelatin by Gel Permcation Chromatography (II), 1984, vol. 47, No. 4, pp. 237-247, ISSN 1884-5932 Abstract, p. 242 Left-column Lines 4-13, Figure 5, 13, Table 2.

International Search Report for PCT/JP2022/032703 dated Nov. 1, 2022.

Takashi Ohno et al, Determination of Molecular Weight Distribution of Gelatin by Gel Permeation Chromatography (III), 1984, vol. 47, No. 4, pp. 237-247, ISSN 1884-5932 Abstract, p. 242 Left-column Lines 4-13, Figure 5, 13, Table 2.

International Search Report for PCT/JP2022/032793 dated Nov. 1, 2022.

Extended European Search Report dated Dec. 18, 2025 in Application No. 22895194.3.

Denis et al., "Molecular weight determination of hydrolyzed collagens", Food Hydrocolloids, 2008, pp. 989-994, vol. 22.

Berteau et al., "Evaluation of the impact of viscosity, injection vol. and injection flow rate on subcutaneous injection tolerance", Medical Devises: Evidence and Research, 2015, pp. 473-484, vol. 8.

*Primary Examiner* — Bruck Kifle
(74) *Attorney, Agent, or Firm* — Sughrue Mion, PLLC

(57) ABSTRACT

A leakage inhibiting agent includes a gelatin hydrolysate having a weight average molecular weight of 5000 or lees, wherein a degree of viscosity at 25° C. of a first solution obtained by dissolving the gelatin hydrolysate in phosphate buffered saline and adjusting the concentration of the gelatin hydrolysate to 40% by mans is 20 mPa·s or less.

10 Claims, No Drawings

LEAKAGE INHIBITING AGENT FOR LOCAL INJECTION PREPARATION, LOCAL INJECTION PREPARATION INCLUDING THE SAME, AND METHOD FOR PRODUCING LOCAL INJECTION PREPARATION

This Application is a National Stage of International Application No. PCT/JP2022/032793 filed Aug. 31, 2022, claiming priority based on Japanese Patent Application No. 2021-186121 filed Nov. 16, 2021.

TECHNICAL FIELD

The present invention relates to a leakage inhibiting agent for a local injection preparation, a local injection preparation including the same, and a method for producing the local injection preparation.

BACKGROUND ART

Japanese Patent Laying-Open No. 2007-001989 (PTL 1) and Japanese Patent Laying-Open No. 2001-192336 (PTL 2) disclose an injection preparation that prolongs the local residence time of an active ingredient to cause mucosal elevation in order to contribute, for example, to the resection of an affected area. In order to prolong the local residence time of the active ingredient, it is at least required to reduce the liquid leakage of the injection preparation from the affected area, that is, to inhibit the leakage of the injection preparation.

It is known that it is effective to impart viscosity to an injection preparation solvent used to dissolve or disperse the active ingredient in order to inhibit the leakage of the injection preparation. PTL 1 above states that it is effective to adjust the degree of viscosity of an aqueous solution including hyaluronic acid, which is the active ingredient in the injection preparation, to 40 mPa·s or more in order to inhibit the leakage of the injection preparation. PTL 2 above teaches the use of 0.2 to 1.0% by mass of hyaluronic acid having a weight average molecular weight of 600000 to 1200000.

CITATION LIST

Patent Literature

PTL 1: Japanese Patent Laying-Open No. 2007-001989
PTL 2: Japanese Patent Laying-Open No. 2001-192336

SUMMARY OF INVENTION

Technical Problem

However, the present inventors prepared a 0.2% by mass hyaluronic acid aqueous solution by using hyaluronic acid having a weight average molecular weight of 900000 and found that the degree of viscosity of the aqueous solution was 16.7 mPa·s and that when the aqueous solution is injected by using a syringe including an injection needle having an outer diameter of 27 G, the leakage inhibiting effect described above cannot be obtained. On the other hand, it is known that when an injection preparation has a high viscosity, a high back pressure is required and this makes it difficult to carry out appropriate injection, thus making it difficult to retain most of the injection preparation in an affected area (target site). Therefore, an injection preparation that can inhibit the leakage of the injection preparation even if it has a low viscosity or degree of viscosity that does not require a high back pressure for injection and that can retain the injection preparation at a target site has not yet been realized, and the development thereof is eagerly awaited.

In view of the above circumstances, an object of the present invention is to provide a leakage inhibiting agent for a local injection preparation that can inhibit the leakage of an injection preparation and can retain an active ingredient and the like at a target site, a local injection preparation including the same, and a method for producing the local injection preparation.

Solution to Problem

The present inventors have made intensive studies in order to achieve the above object and arrived at the present invention. First, the present inventors have noticed that the degree of viscosity is maintained at a relatively low level even when a gelatin hydrolysate having a predetermined weight average molecular weight is included at a high concentration in a water-based solvent. Next, the present inventors have prepared a local injection preparation by using a leakage inhibiting agent including the gelatin hydrolysate and found that the local injection preparation exhibits a leakage inhibiting effect and thus can retain the active ingredient well at a target site, and completed the present invention.

That is, the present invention has the following features.
[1] A leakage inhibiting agent for a local injection preparation according to the present invention includes a gelatin hydrolysate having a weight average molecular weight of 5000 or less, and a degree of viscosity at 25° C. of a first solution obtained by dissolving the gelatin hydrolysate in phosphate buffered saline and adjusting the concentration of the gelatin hydrolysate to 40% by mass is 20 mPa·s or less.
[2] The leakage inhibiting agent preferably consists of the gelatin hydrolysate.
[3] The leakage inhibiting agent is preferably for a local injection preparation with which a syringe including an injection needle having an outer diameter of 23 G or more and 37 G or less is filled.
[4] The leakage inhibiting agent is preferably for a local injection preparation with which a syringe including an injection needle having an outer diameter of 23 G or more and 27 G or less is filled.
[5] A local injection preparation according to the present invention includes the leakage inhibiting agent.
[6] Preferably, the local injection preparation includes 5% by mass or more and 40% by mass or less of the leakage inhibiting agent, and the degree of viscosity at 25° C. of the local injection preparation is 2 mPa·s or more and 20 mPa·s or less.
[7] Preferably, the local injection preparation includes 5% by mass or more and 40% by mass or less of the leakage inhibiting agent, and the degree of viscosity at 25° C. of the local injection preparation is 2 mPa·s or more and 10 mPa·s or less.
[8] The local injection preparation preferably includes 5% by mass or more and 40% by mass or less of the leakage inhibiting agent, and the degree of viscosity at 25° C. of the local injection preparation is 8 mPa·s or more and 20 mPa·s or less.
[9] A method for producing a local injection preparation according to the present invention is a method for producing the local injection preparation, including preparing the leakage inhibiting agent, a water-based solvent, and an active ingredient; and obtaining the local injection preparation by mixing the leakage inhibiting agent and the active ingredient into the water-based solvent at 1° C. or more and 30° C. or less.

[10] The obtaining a local injection preparation is preferably any of obtaining the local injection preparation by mixing the leakage inhibiting agent into the water-based solvent to obtain a first injection precursor and then mixing the active ingredient into the first injection precursor, or obtaining the local injection preparation by mixing the active ingredient into the water-based solvent to obtain a second injection precursor and then mixing the leakage inhibiting agent into the second injection precursor, or obtaining the local injection preparation by simultaneously mixing the leakage inhibiting agent and the active ingredient into the water-based solvent.

Advantageous Effects of Invention

According to the present invention, it is possible to provide a leakage inhibiting agent for a local injection preparation that can inhibit the leakage of an injection preparation and can retain an active ingredient and the like at a target site, a local injection preparation including the same, and a method for producing the local injection preparation.

DESCRIPTION OF EMBODIMENTS

Hereinafter, the embodiment according to the present invention (hereinafter also referred to as "the present embodiment") will be described in more detail. As used herein, the expression of a range in the format "A to B" means the upper limit and the lower limit of the range (that is, A or more and B or less), and when no unit is written for A and a unit is only written in B, the unit for A and the unit for B are the same. As used herein, the term "gelatin" may be used when referring to each of the substance name, a gelatin gel, and a gelatin solution. Further, the term "gelatin hydrolysate" may also be used when referring to a gelatin hydrolysate solution, as in the case of the gelatin.

As used herein, the "local injection" means an injection method in general, excluding injection involving inserting a needle into a blood vessel such as intravenous injection, and means, for example, intradermal injection, subcutaneous injection, intramuscular injection, injection into or around a nerve, injection into a soft tissue, and injection into a joint such as a knee or a facet joint of the spine. As used herein, the category of the "first solution" obtained by dissolving a gelatin hydrolysate in phosphate buffered saline and adjusting the concentration of the gelatin hydrolysate to 40% by mass includes not only a liquid in a state in which the entire amount of the gelatin hydrolysate is dissolved in phosphate buffered saline, but also a liquid in a state in which a slight amount of the gelatin hydrolysate is dispersed without being dissolved. For example, when the gelatin hydrolysate has the form of a chemically modified form or a derivative described later, the "first solution" may be a liquid in a state in which the gelatin hydrolysate is dispersed without being dissolved.

[Leakage Inhibiting Agent for Local Injection Preparation]

The leakage inhibiting agent for a local injection preparation according to the present embodiment includes a gelatin hydrolysate having a weight average molecular weight of 5000 or less. Further, the degree of viscosity at 25° C. of the first solution obtained by dissolving the gelatin hydrolysate in phosphate buffered saline (hereinafter also referred to as "PBS buffer") and adjusting the concentration of the gelatin hydrolysate to 40% by mass is 20 mPa·s or less. The leakage inhibiting agent preferably consists of the gelatin hydrolysate. By having such characteristics, the leakage inhibiting agent can inhibit the leakage of the local injection preparation from a target site and thus can retain the local injection preparation at the target site. Further, even when the leakage inhibiting agent is included in a water-based solvent at a high concentration, the degree of viscosity can be maintained at a relatively low level, and thus it becomes possible to easily prepare a local injection preparation having the leakage inhibiting effect described above.

<Gelatin Hydrolysate>

The leakage inhibiting agent includes a gelatin hydrolysate having a weight average molecular weight of 5000 or less as described above. As used herein, the "gelatin hydrolysate" refers to a peptide aggregate (hydrolysate) obtained by hydrolyzing both or either one of gelatin and collagen. That is, the "gelatin hydrolysate" means the equivalent of a peptide aggregate commonly referred to as a collagen peptide or a collagen hydrolysate. Among the same, the gelatin hydrolysate included in the leakage inhibiting agent has a weight average molecular weight (5000 or less) as described above. Further, the gelatin hydrolysate means a peptide aggregate as described above, and thus has the same characteristics as collagen and gelatin, such as having a primary structure in which glycine is repeated every three residues in the amino acid sequence that constitutes a peptide chain.

As used herein, the "gelatin" means a polypeptide in which the triple helical structure of collagen is unfolded by heat denaturation, acid denaturation, or the like, a chemically modified form thereof, and a pharmaceutically acceptable salt thereof.

Specifically, the gelatin can be obtained by subjecting collagen derived from at least one selected from the group consisting of groups 1 to 6 below to a conventionally known treatment such as degreasing treatment, decalcification treatment, acid or alkali treatment, or hot water extraction treatment. The gelatin may be a polypeptide obtained by a fermentation method using a microorganism, or a recombinant polypeptide or a synthesized polypeptide obtained by a chemical synthesis or a genetic recombination. In addition, the "collagen" refers to a protein derived from the extracellular matrix in the skin or the like of vertebrates, which are classified into groups 1 to 6 below. The collagen has a right-handed helical structure consisting of three peptide chains, and the amino acid residues constituting the peptide chains have a primary structure in which glycine residues are repeated every three residues (so-called collagen-like sequence).

Group 1: A group consisting of a hide, a skin, a bone, a cartilage, and a tendon of a cow Group 2: A group consisting of a hide, a skin, a bone, a cartilage, and a tendon of a pig Group 3: A group consisting of a hide, a skin, a bone, a cartilage, and a tendon of a sheep Group 4: A group consisting of a hide, a skin, a bone, a cartilage, and a tendon of a chicken Group 5: A group consisting of a hide, a skin, a bone, a cartilage, and a tendon of an ostrich Group 6: A group consisting of a bone, a skin, and a scale of a fish.

Here, the "chemically modified form" of the polypeptide (gelatin) means a polypeptide in which an amino group, a carboxyl group, a hydroxy group, a thiol group, or the like of an amino acid residue constituting the gelatin is chemically modified. The chemically modified gelatin can have a changed solubility in water, isoelectric point thereof, or the like. Specifically, a chemical modification such as O-acetylation can be carried out on the hydroxy group of a hydroxyproline residue in gelatin. A chemical modification such as esterification or amidation can be carried out on an α-carboxyl group of a glycine residue in gelatin. A chemical modification such as polypeptidylation, succinylation, maleylation, acetylation, deamination, benzoylation, alkylsulfonylation, allylsulfonylation, dinitrophenylation, trinitrophenylation, carbamylation, phenylcarbamylation, or thiolation can be carried out on an α-amino group of a proline residue in gelatin.

A conventionally known chemical modification method can be applied to specific means and a treatment condition for a chemical modification of gelatin. For a chemical modification of the hydroxy group of a hydroxyproline residue, for example, O-acetylation thereof can be carried out, for example, by causing acetic anhydride to act in an aqueous solvent or in a nonaqueous solvent. For a chemical modification of the α-carboxyl group of a glycine residue, for example, esterification thereof can be carried out, for example, by passing dry hydrogen chloride gas after suspension in methanol. For a chemical modification of the α-carboxyl group of a glycine residue, amidation thereof can be carried out by causing carbodiimide or the like to act.

Further, the "derivative" of the polypeptide (gelatin) may include a gelatin derivative obtained by introducing a functional group into the gelatin, a copolymer of the gelatin with lactic acid, glycolic acid, or the like, a copolymer of the gelatin with polyethylene glycol or propylene glycol, or the like. Examples of the gelatin derivative include a derivative obtained by introducing a functional group such as a guanidyl group, a thiol group, an amino group, a carboxyl group, a sulfuric acid group, a phosphoric acid group, an alkyl group, an acyl group, a phenyl group, or a benzyl group into the gelatin.

The "pharmaceutically acceptable salt" of the polypeptide (gelatin) means a salt that is pharmaceutically acceptable and has the desired activity (for example, gelling ability) of the original polypeptide (gelatin). Examples of the pharmaceutically acceptable salt include an inorganic acid salt such as a hydrochloride, a sulfate, a phosphate, or a hydrobromide; an organic acid salt such as an acetate, a methanesulfonate, a benzenesulfonate, a p-toluenesulfonate, a succinate, an oxalate, a fumarate, and a maleate; an inorganic base salt such as a sodium salt, a potassium salt, and a calcium salt; and an organic base salt such as a triethylammonium salt. A specific peptide in gelatin can be converted into a pharmaceutically acceptable salt according to a conventional method.

Gelatin is a polypeptide derived from collagen possessed by many organisms and thus has excellent biocompatibility. Because of this, the gelatin hydrolysate obtained by hydrolyzing the collagen and gelatin also has excellent biocompatibility and is suitable as a component (leakage inhibiting agent) included in a local injection preparation for medicinal use.

When the gelatin hydrolysate is dissolved in a solvent (for example, water), the gelatin hydrolysate does not gel at room temperature around 25° C. or even in an environment at 2 to 8° C., and maintains the sol state thereof. Therefore, the leakage inhibiting agent does not require a heating operation for solation when used at room temperature around 25° C. In the present embodiment, the "sol" means a dispersion system consisting of a dispersoid and a dispersion medium, in which the dispersion medium is liquid. The "gel" means a dispersion system consisting of a dispersoid and a dispersion medium, in which the dispersoid forms a crosslinked structure and the dispersion system as a whole has lost the fluidity thereof.

The gelatin hydrolysate can be obtained by hydrolyzing both or either one of gelatin and collagen as described above. In this case, the "hydrolysis" includes hydrolysis using an acid, hydrolysis using a base, hydrolysis using an enzyme, and hydrolysis using heat. From the viewpoint of preventing contamination with an impurity, the gelatin hydrolysate is preferably obtained by hydrolysis using heat. Further, when both or either one of gelatin and collagen is hydrolyzed by using an enzyme, examples of the enzyme include a collagenase, a thiol protease, a serine protease, an acid protease, an alkaline protease, and a metalloprotease. The enzymes described above can be used singly or in combinations of a plurality thereof. Examples of the thiol protease include plant-derived chymopapain, papain, bromelain, and ficin, and animal-derived cathepsin and calcium-dependent protease. Examples of the serine protease include trypsin and cathepsin D. Examples of the acid protease include pepsin and chymotrypsin.

In consideration of the use of the gelatin hydrolysate in a medicament, it is preferable to use an enzyme other than an enzyme derived from a pathogenic microorganism (for example, an enzyme derived from a non-pathogenic microorganism). Examples of the non-pathogenic microorganism from which the above enzymes are derived include *Bacillus licheniformis, Bacillus subtilis, Aspergillus oryzae, Streptomyces*, and *Bacillus amyloliquefaciens*. As the enzyme, an enzyme derived from one of the non-pathogenic microorganisms described above may be used, or enzymes derived from a plurality of the non-pathogenic microorganisms described above may be used in combination. A conventionally known method may be used as a specific method for an enzymatic treatment.

The gelatin hydrolysate is preferably a liquid or a powder. When the gelatin hydrolysate is a liquid, a local injection preparation can be easily prepared from the leakage inhibiting agent, and an active ingredient and a water-based solvent, which will be described later. When the gelatin hydrolysate is a powder, a local injection preparation can be easily prepared by dissolving or dispersing the leakage inhibiting agent in a water-based solvent to prepare an injection preparation solvent, and adding an active ingredient thereto. The gelatin hydrolysate can be obtained as a liquid by hydrolyzing both or either one of gelatin and collagen by the method described above, followed by purification. Further, it is possible to obtain the gelatin hydrolysate as a powder by heat-drying or freeze-drying the liquid by known means.

(Weight Average Molecular Weight)

The gelatin hydrolysate has a weight average molecular weight of 5000 or less. The gelatin hydrolysate preferably has a weight average molecular weight of 3000 or more and 5000 or less. Thereby, the leakage inhibiting agent maintains the degree of viscosity at a relatively low level even when included in a water-based solvent at a high concentration, and thus in the case of application as a local injection preparation, although no high back pressure is required, it is possible to exhibit the leakage inhibiting effect at a target site. Although the detailed mechanism is unknown, it is presumed that when the weight average molecular weight of the gelatin hydrolysate is 5000 or less, the gelatin molecules are degraded into a moderate length, and even at a high concentration, the molecules are less likely to entangle, and thus the degree of viscosity can be maintained at a relatively low level even when the gelatin hydrolysate is included in a water-based solvent at a high concentration. This makes it possible to easily prepare a local injection preparation having the leakage inhibiting effect.

When the weight average molecular weight of the gelatin hydrolysate exceeds 5000, the degree of viscosity may increase beyond the allowable range. The lower limit of the weight average molecular weight of the gelatin hydrolysate is not particularly limited, and for example, the weight average molecular weight of the gelatin hydrolysate is preferably 500 or more.

The weight average molecular weight of the gelatin hydrolysate can be determined by carrying out gel filtration chromatography under the following measurement conditions.

Instrument: High performance liquid chromatography (HPLC) (manufactured by Tosoh Corporation)

Column: TSKGel (registered trademark) G2000SWXL

Column temperature: 30° C.

Eluent: 40% by mass acetonitrile (including 0.05% by mass TFA)

Flow rate: 0.5 mL/min

Injection volume: 10 μL

Detection: UV 220 nm

Molecular weight markers: Use the following three types
    Aprotinin Mw: 6512
    Bacitracin Mw: 1423
    Gly-Gly-Tyr-Arg Mw: 451.

Specifically, a leakage inhibiting agent including the gelatin hydrolysate is added in an amount corresponding to 0.5 g to about 100 ml of distilled water, stirred, and then filtered by using a 0.2 μm filter to prepare a sample for weight average molecular weight measurement (object to be measured). The weight average molecular weight of the gelatin hydrolysate can be determined by measuring the object to be measured under the gel filtration chromatography conditions described above.

(Isoelectric Point)

The gelatin hydrolysate has an isoelectric point of preferably pH 4.0 or more and 5.5 or less, and more preferably pH 4.0 or more and 4.7 or less. In order to satisfy this condition, the gelatin hydrolysate is preferably a hydrolysate of alkali-treated gelatin having an isoelectric point of about pH 4.8 to 5.5. That is, the gelatin hydrolysate is preferably a hydrolysate of alkali-treated gelatin. In general, gelatin obtained by treating collagen by using an inorganic acid is referred to as acid-treated gelatin, and gelatin obtained by treating collagen by using an inorganic base is referred to as alkali-treated gelatin. Alkali-treated gelatin can be specifically obtained by treating collagen by using an inorganic base such as sodium hydroxide, calcium hydroxide, or potassium hydroxide.

The leakage inhibiting agent for a local injection preparation according to the present embodiment may be applied to a local injection preparation including a virus or a component such as a DNA or RNA fragment of the virus or a protein of the virus, as described later. In that case, when the gelatin hydrolysate included in the leakage inhibiting agent exhibits the pH of the isoelectric point as described above, the gelatin hydrolysate in the local injection preparation can inhibit the aggregation of the above component of the virus and thus can inhibit a decrease in virus titer. Although the detailed mechanism is unknown, the gelatin hydrolysate exhibiting the pH of the isoelectric point possessed by alkali-treated gelatin exhibits a negative charge as a whole, but has both a positively charged site and a negatively charged site in the molecule. Because of this, the gelatin hydrolysate can bind to the virus by exhibiting a weak electrostatic interaction with the above component in the virus at the positively charged site. On the other hand, at the negatively charged site in the gelatin hydrolysate, the virus and a different peptide chain that constitutes the gelatin hydrolysate repel with each other. From the above, it is presumed that the gelatin hydrolysate can stabilize the virus in the local injection preparation while inhibiting the aggregation of the virus.

The pH of the isoelectric point of the gelatin hydrolysate can be determined by measuring the pH of the isoelectric point of both or either one of gelatin and collagen, which are raw materials of the gelatin hydrolysate, by using a conventionally known method, and it is preferable to use the following method for measuring the isoelectric point using the zeta potential as an index, because the isoelectric point value can be determined more accurately. That is, first, the gelatin hydrolysate to be measured is dissolved in an acetate buffer solution (pH 4.0 to 5.5) to obtain a 0.4 w/v % solution to be measured. Next, the solution to be measured is filtered through a 0.22 μm filter (manufactured by Merck), and then a capillary cell is filled with 0.8 mL of the solution to be measured while preventing an air bubble from entering the same. Subsequently, the capillary cell filled with the solution to be measured is set in a zeta potential measuring apparatus (manufactured by Malvern Panalytical Ltd) to measure the zeta potential at each pH at 25° C. At this time, the pH value at which the zeta potential becomes 0 can be determined as the isoelectric point of the solution to be measured (the gelatin hydrolysate to be measured).

(Concentration)

The concentration of the gelatin hydrolysate in the leakage inhibiting agent is not particularly limited, and from the viewpoint of facilitating the preparation of a local injection preparation, the concentration is preferably 25% by mass or more and 100% by mass or less. If the concentration of the gelatin hydrolysate in the leakage inhibiting agent is less than 25% by mass, when preparing a local injection preparation, a large amount of the leakage inhibiting agent is required in order to exhibit the leakage inhibiting effect, which poses a problem. The concentration of the gelatin hydrolysate in the leakage inhibiting agent is more preferably 50% by mass or more and 100% by mass or less, and also preferably, the concentration of the gelatin hydrolysate in the leakage inhibiting agent is 100% by mass, that is, the leakage control agent consists of the gelatin hydrolysate. Examples of a component other than the gelatin hydrolysate included as the leakage inhibiting agent include a component other than the gelatin hydrolysate derived from gelatin or collagen, which are raw materials, a diluent, a binder (syrup, gum arabic, sorbitol, tragacanth, or polyvinylpyrrolidone), an excipient (lactose, sucrose, corn starch, potassium phosphate, sorbitol, or glycine), a lubricant (magnesium stearate, talc, polyethylene glycol, or silica), a disintegrant (potato starch), and a wetting agent (sodium lauryl sulfate). The concentration of the gelatin hydrolysate in the leakage inhibiting agent can be measured by a known method such as hydroxyproline quantification.

<First Solution>

In the leakage inhibiting agent for a local injection preparation according to the present embodiment, the degree of viscosity at 25° C. of the first solution obtained by dissolving the gelatin hydrolysate in PBS buffer and adjusting the concentration of the gelatin hydrolysate to 40% by mass is 20 mPa·s or less. That is, the first solution is prepared as an aqueous solution obtained by dissolving the gelatin hydrolysate included in the leakage inhibiting agent in PBS buffer and adjusting the concentration of the gelatin hydrolysate to 40% by mass, or a dispersion in which the concentration of the gelatin hydrolysate is 40% by mass, and a slight amount of the gelatin hydrolysate is dispersed without being dissolved. Further, the degree of viscosity at 25° C. of the first solution is 20 mPa·s or less although the first solution includes 40% by mass of the gelatin hydrolysate. From the above, it is understood that the degree of viscosity of the leakage inhibiting agent exhibits a relatively low level even when a water-based solvent includes the gelatin hydrolysate at a high concentration.

Because of this, the local injection preparation including the leakage inhibiting agent can exhibit the effect of inhibiting leakage from a target site although no high back pressure is required at the time of injection. In a local injection preparation including a leakage inhibiting agent that causes the degree of viscosity at 25° C. of the first solution to be 20 mPa·s or less, it is possible to further exhibit the leakage inhibiting effect by appropriately selecting the size of the outer diameter of the injection needle applied to a syringe to be filled with the local injection preparation. The lower limit value of the degree of viscosity at 25° C. of the first solution should not be particularly limited, and from the viewpoint of further exhibiting the effect of inhibiting leakage from the target site of the local injection preparation including the leakage inhibiting agent, the lower limit value is preferably 2.5 mPa·s or more. In addition, even for a gelatin hydrolysate having a weight average molecular weight of 5000 or less, it is presumed that in a gelatin hydrolysate including a polymer component in an amount equal to or more than a certain amount due to a fairly wide molecular weight distribution, polymer molecules entangle with each other, resulting in an increase in viscosity. Because of this, the degree of viscosity at 25° C. of the first solution obtained by dissolving such a gelatin hydrolysate in PBS buffer and adjusting the concentration thereof to 40% by mass may exceed 20 mPa·s.

The degree of viscosity of the first solution can be determined by measurement at 25° C. using a rheometer (trade name (product number): "MCE302", Anton Paar Japan K.K., cone plate R25, 1°, shear rate of 200 s$^{-1}$). In the case of the degree of viscosity of the first solution, after confirming that the value is stable from the start of measurement, the value after 1 minute from the start of measurement is adopted.

<Use>

The leakage inhibiting agent for a local injection preparation according to the present embodiment is for a local injection preparation. In particular, the leakage inhibiting agent is preferably for a local injection preparation with which a syringe including an injection needle having an outer diameter of 23 G or more and 37 G or less is filled. The leakage inhibiting agent is also preferably for a local injection preparation with which a syringe including an injection needle having an outer diameter of 23 G or more and 27 G or less is filled. As described above, the term local injection refers to, for example, intradermal injection, subcutaneous injection, intramuscular injection, injection into or around a nerve, injection into a soft tissue, and injection into a joint such as a knee or a facet joint of the spine, and means an injection method in general, excluding injection involving inserting a needle into a blood vessel such as intravenous injection. Therefore, the leakage inhibiting agent has, as a hitherto unknown property of a gelatin hydrolysate, that is, an unknown property, the action of being able to inhibit the leakage of the injection preparation from a target site such as an intradermal one, a subcutaneous one, an intramuscular one, a nerve or a surrounding area thereof, a soft tissue, or an intra-articular one such as a knee and a facet joint of the spine and cause the injection preparation to be retained at the target site. Therefore, the leakage inhibiting agent can provide an effective new use of a gelatin hydrolysate.

Here, the "injection needle having an outer diameter of 23 G or more and 37 G or less" specifically refers to an injection needle having an outer diameter of 0.08±0.02 mm to 0.64±0.02 mm. That is, the 23 G injection needle has an outer diameter of 0.64±0.02 mm, the 24 G injection needle has an outer diameter of 0.56±0.02 mm, the 25 G injection needle has an outer diameter of 0.51±0.02 mm, the 26 G injection needle has an outer diameter of 0.46±0.02 mm, and the 27 G injection needle has an outer diameter of 0.41±0.02 mm. The 28 G injection needle has an outer diameter of 0.36±0.02 mm, the 29 G injection needle has an outer diameter of 0.33±0.02 mm, the 30 G injection needle has an outer diameter of 0.31±0.02 mm, the 31 G injection needle has an outer diameter of 0.27±0.02 mm, and the 32 G injection needle has an outer diameter of 0.23±0.02 mm. The 33 G injection needle has an outer diameter of 0.20±0.02 mm, the 35 G injection needle has an outer diameter of 0.15±0.02 mm, the 36 G injection needle has an outer diameter of 0.10±0.02 mm, and the 37 G injection needle has an outer diameter of 0.08±0.02 mm. Therefore, the leakage inhibiting agent can inhibit the leakage of an active ingredient in a local injection preparation from a target site and can retain the active ingredient at the target site, in various uses in which a syringe including an injection needle having an outer diameter of 23 G or more and 37 G or less is applied. The leakage inhibiting agent is particularly suitable for a use such as intratumoral administration to which a syringe including an injection needle having an outer diameter of 23 G is applied and general intramuscular injection, and a use such as cell transplantation into a soft tissue to which a syringe including an injection needle having an outer diameter of 27 G is applied and general intradermal injection. Further, the leakage inhibiting agent can also be applied to an ultra-fine injection needle as used in ophthalmology (for example, 37 G, outer diameter of 0.08 mm, inner diameter of 0.05 mm).

[Local Injection Preparation]

The local injection preparation according to the present embodiment includes the leakage inhibiting agent. Thereby, the local injection preparation can inhibit the leakage of an active ingredient from a target site and retain the active ingredient at the target site. In addition to the leakage inhibiting agent, the local injection preparation can include an active ingredient such as an agent, a virus, a cell, or a different physiologically active substance, a water-based solvent that serves as a medium for dissolving or dispersing the leakage inhibiting agent, and the like.

<Active Ingredient>

The local injection preparation according to the present embodiment can include, as an active ingredient, an agent, a virus, a component such as a DNA or RNA fragment of the virus, a protein of the virus (hereinafter also referred to as a "virus or the like"), a cell, or a different physiologically active substance. As long as the agent is applicable as an injection preparation, the agent may be an agent including an inorganic compound, an agent including a compound that can be produced by an organic synthesis reaction, or an agent including a compound extracted from a natural product or the like. As the agent, any of a synthetic low-molecular preparation having a molecular weight of less than 500 Da, a nucleic acid preparation or peptide preparation having a molecular weight of about 500 to 5000 Da, and a protein preparation having a molecular weight of tens of thousands of Da or more can be applied. The agent may be a derivative of a molecule exhibiting activity, a precursor of the molecule, or a salt of the molecule. Here, as used herein, the "derivative" of a molecule means a substance formed by modifying a part of the intramolecular structure of the molecule by introducing a functional group into the molecule or carrying out an oxidation-reduction reaction on the molecule. The "precursor" of a molecule means a substance from which the molecule is generated by biosynthesis or synthesis. The "salt" of a molecule means a salt formed by treating the molecule with an acid or a base while maintaining the activity of the molecule itself.

As the virus, any of an enveloped DNA virus, a non-enveloped DNA virus, an enveloped RNA virus, and a non-enveloped RNA virus can be used for the local injection preparation. In addition, a component such as DNA or RNA fragments of these viruses or proteins of these viruses can also be used for the local injection preparation. As described above, the gelatin hydrolysate included in the local injection preparation can inhibit the aggregation of the virus, and thus can inhibit a decrease in virus titer, and thereby the stability of a local injection preparation including a virus or the above component of the virus can be improved at both a refrigeration temperature (2 to 8° C.) and at room temperature around 25° C.

Examples of the different physiologically active substance include various cells (including both a stem cell and a differentiated cell), a growth factor, a differentiation factor, a hormone, a chemokine, a cytokine, a cell adhesion molecule, a chemotactic factor, an enzyme, an enzyme inhibitor, a coenzyme (a vitamin), a mineral, fat, lipid, a stabilizer, and a preservative. Any of these physiologically active substances can be used for the local injection preparation.

<Water-Based Solvent>

The local injection preparation according to the present embodiment can include a water-based solvent as described above. As used herein, the term "water-based solvent" refers to a medium that dissolves or disperses the leakage inhibiting agent, and means a medium that can include a component other than water, such as an amino acid, a sugar, and a salt having a buffering action, which will be described later. For example, the water-based solvent may be a buffer solution including a salt having a buffering action. Specifically, the water-based solvent may be GTS buffer. A water-based solvent can improve the stability of the local injection preparation.

(Salt Having Buffering Action)

Examples of the salt having a buffering action include sodium phosphate, potassium phosphate, calcium phosphate, magnesium phosphate, sodium hydrogen phosphate, potassium hydrogen phosphate, calcium hydrogen phosphate, magnesium hydrogen phosphate, sodium chloride, and potassium chloride. The water-based solvent may include only one of the above salts having a buffering action, or may include two or more thereof in combination. Examples of a water-based solvent including such a salt having a buffering action include the GTS buffer, PBS buffer, Tris buffer, HEPES buffer, and citrate buffer.

(Amino Acid)

The water-based solvent preferably includes at least one amino acid selected from the group consisting of methionine, arginine, tryptophan, glutamine, and glutamic acid. The water-based solvent may include only one amino acid selected from the group consisting thereof, or may include two or more in combination. The water-based solvent more preferably includes both amino acids or either one of methionine and arginine. The local injection preparation can contribute to improved stability even when it includes an amino acid.

(Sugar)

The water-based solvent preferably includes at least one sugar selected from the group consisting of sucrose, lactose, sorbitol, inositol, trehalose, mannitol, maltitol, xylitol, erythritol, and glycerol. The water-based solvent may include only one sugar selected from the group consisting thereof, or may include two or more in combination. The water-based solvent more preferably includes at least one of sucrose, lactose, and sorbitol. The local injection preparation can contribute to improved stability even when it includes a sugar. As used herein, a compound included in the "sugar" includes not only an organic compound generally classified as a sugar, but also an organic compound classified as a sugar alcohol. The organic compounds classified as a sugar alcohol in the above group of sugars are the above sorbitol, mannitol, maltitol, xylitol, erythritol, and glycerol.

(Concentration of Leakage Inhibiting Agent Included in Local Injection Preparation and Degree of Viscosity at 25° C. of Local Injection Preparation)

The local injection preparation preferably includes 5% by mass or more and 40% by mass or less of the leakage inhibiting agent. In this case, the degree of viscosity at 25° C. of the local injection preparation is preferably 2 mPa·s or more and 20 mPa·s or less. When the concentration of the leakage inhibiting agent included in the local injection preparation is less than 5% by mass, it becomes difficult to obtain a predetermined degree of viscosity, and thus it becomes difficult to exhibit a desired leakage inhibiting effect. When the concentration of the leakage inhibiting agent included in the local injection preparation exceeds 40% by mass, the degree of viscosity may increase beyond the allowable range. The concentration of the leakage inhibiting agent included in the local injection preparation is more preferably 10% by mass or more and 40% by mass or less, more further preferably 20% by mass or more and 40% by mass or less, and also more further preferably more than 20% by mass and less than 40% by mass. The concentration of the leakage inhibiting agent in the local injection preparation can be measured by using a known method such as hydroxyproline quantification by regarding the leakage inhibiting agent as substantially consisting of the gelatin hydrolysate.

Also preferably, the local injection preparation includes 5% by mass or more and 40% by mass or less of the leakage inhibiting agent, and the degree of viscosity at 25° C. of the local injection preparation is 2 mPa·s or more and 10 mPa·s or less. Such a local injection preparation can retain the active ingredient in the local injection preparation extremely well at a target site without leakage when a syringe including an injection needle having an outer diameter of 27 G is filled therewith. The local injection preparation more preferably includes 10% by mass or more and 40% by mass or less of the leakage inhibiting agent when a syringe including an injection needle having an outer diameter of 27 G is filled therewith.

Further, also preferably, the local injection preparation includes 5% by mass or more and 40% by mass or less of the leakage inhibiting agent, and the degree of viscosity at 25° C. of the local injection preparation is 8 mPa·s or more and 20 mPa·s or less. Such a local injection preparation can retain the active ingredient in the local injection preparation extremely well at a target site without leakage when a syringe including an injection needle having an outer diameter of 23 G is filled therewith. The local injection preparation more preferably includes 10% by mass or more and 40% by mass or less of the leakage inhibiting agent when a syringe including an injection needle having an outer diameter of 23 G is filled therewith.

Action and Effect

The local injection preparation according to the present embodiment can include a leakage inhibiting agent, an active ingredient, and a water-based solvent as described above, and in that case, can retain the active ingredient at a target site without leakage. In particular, when the local injection preparation includes a virus or the like as an active ingredient, the local injection preparation can inhibit the aggregation of the virus or the like in the local injection preparation, thereby also inhibiting a decrease in virus titer, and thus the stability of the local injection preparation can be improved at both a refrigeration temperature (2 to 8° C.) and room temperature around 25° C. Further, according to a study by the present inventors, the local injection preparation is expected to be also suitable for a use such as cell therapy because the local injection preparation is also excellent in cell retention and cell ejection as described later.

[Method for Producing Local Injection Preparation]

The local injection preparation according to the present embodiment can preferably be obtained by the following method. That is, the method for producing the local injection preparation according to the present embodiment preferably includes preparing the leakage inhibiting agent, a water-based solvent, and an active ingredient (first step), and obtaining the local injection preparation by mixing the leakage inhibiting agent and the active ingredient into the water-based solvent at 1° C. or more and 30° C. or less (second step). The above "active ingredient" and "water-based solvent" have the same meanings as the "active ingredient" and "water-based solvent" described in the above section [Local injection preparation], and no redundant description will be repeated.

(First Step)

The first step is preparing the leakage inhibiting agent, a water-based solvent, and an active ingredient. The gelatin hydrolysate included in the leakage inhibiting agent can be obtained by hydrolyzing both or either one of gelatin and collagen and adjusting the weight average molecular weight to 5000 or less as described above. The leakage inhibiting agent can be prepared by mixing the gelatin hydrolysate and a different component at a mass ratio such that the concentration of the gelatin hydrolysate is 25% by mass or more and 100% by mass or less. A conventionally known method can be used as a specific method for mixing the gelatin hydrolysate and the different component. For example, when the water-based solvent includes a salt having a buffering action, the water-based solvent can be prepared by a conventionally known method such as adding the salt to ion exchanged water in such a way as to obtain a predetermined concentration. The active ingredient can be prepared by a conventionally known method for preparing an agent, a virus or the like, or a different physiologically active substance.

(Second Step)

The second step is obtaining the local injection preparation by mixing the leakage inhibiting agent and the active ingredient into the water-based solvent at 1° C. or more and 30° C. or less. In the second step, the leakage inhibiting agent and the active ingredient can be mixed into the water-based solvent at a temperature of 1° C. or more and 30° C. or less to prepare the local injection preparation, and thus the local injection preparation can be obtained very easily. In the second step, the temperature at which the leakage inhibiting agent, the active ingredient, and the water-based solvent are mixed is more preferably 15° C. or more and 25° C. or less, and more further preferably 20° C. or more and 25° C. or less, from the viewpoint of easily obtaining the local injection preparation.

Here, the second step (obtaining the local injection preparation) is preferably any of obtaining the local injection preparation by mixing the leakage inhibiting agent into the water-based solvent to obtain a first injection precursor and then mixing the active ingredient into the first injection precursor (hereinafter also referred to as "step 2a"), or obtaining the local injection preparation by mixing the active ingredient into the water-based solvent to obtain a second injection precursor and then mixing the leakage inhibiting agent into the second injection precursor (hereinafter also referred to as "step 2b"), or obtaining the local injection preparation by simultaneously mixing the leakage inhibiting agent and the active ingredient into the water-based solvent (hereinafter also referred to as "step 2c").

In step 2a, before mixing the active ingredient, the leakage inhibiting agent and the water-based solvent are mixed to obtain the first injection precursor. Therefore, for example, when a compound that hydrolyzes quickly (for example, a compound having a structure of an ester, an amide, a lactam, or the like) or the like is used as the active ingredient, if step 2a is used as the step of obtaining the local injection preparation, a local injection preparation in which the degradation of the active ingredient is minimized can be obtained by mixing the active ingredient into the first injection precursor immediately before local injection.

In step 2b, before mixing the leakage inhibiting agent, the active ingredient and the water-based solvent are mixed to obtain the second injection precursor. Therefore, for example, when a compound or the like whose action is likely to be affected by a change in degree of viscosity due to the leakage inhibiting agent, or the like, is used as the active ingredient, if step 2b is used as the step of obtaining the local injection preparation, a local injection preparation in which the change in action is minimized can be obtained by mixing the leakage inhibiting agent into the second injection precursor immediately before local injection.

In step 2c, the local injection preparation is obtained by simultaneously mixing the leakage inhibiting agent and the active ingredient into the water-based solvent. Therefore, if step 2c is used as the step of obtaining the local injection preparation, the local injection preparation can be obtained in a shorter time and more easily than in step 2a and step 2b.

Action and Effect

The local injection preparation according to the present embodiment can be obtained by the production method described above. By including the leakage inhibiting agent, an active ingredient, and a water-based solvent, the local injection preparation can inhibit the leakage of the active ingredient from a target site and retain the active ingredient and the like at the target site.

EXAMPLES

Hereinafter, the present invention will be described in more detail with reference to Examples, but the present invention is not limited thereto.

[First Test]

In order to evaluate whether or not each sample described below is suitable as the leakage inhibiting agent for a local injection preparation, the following test was carried out. Sample 1 and sample 2 are Examples, and sample 3 and sample 4 are Comparative Examples.

<Preparation of Samples (Leakage Inhibiting Agents)>

(Sample 1)

A pig-derived alkali-treated gelatin hydrolysate having an isoelectric point of pH 5 (trade name: "beMatrix gelatin HG," weight average molecular weight of 4000, manufactured by Nitta Gelatin Inc.) was used as the leakage inhibiting agent of sample 1. Next, various solutions for degree of viscosity measurement including the first solution described above were obtained by dissolving the leakage inhibiting agent in PBS buffer in such a way as to have concentrations shown in Table 1 (1% by mass, 5% by mass, 10% by mass, 20% by mass, 30% by mass, and 40% by mass), respectively. The isoelectric point of the leakage inhibiting agent of sample 1 was measured by the method described above and found to be 4.65.

(Sample 2)

A gelatin hydrolysate was obtained by hydrolyzing a pig-derived alkali-treated gelatin hydrolysate having an isoelectric point of pH 5 (trade name: "beMatrix gelatin LS-H," manufactured by Nitta Gelatin Inc.) by heat such that the weight average molecular weight was 5900, and this was used as the leakage inhibiting agent of sample 4. Next, various solutions for degree of viscosity measurement including the first solution were obtained by dissolving the leakage inhibiting agent in PBS buffer in such a way as to have concentrations shown in Table 1 (20% by mass, 30% by mass, and 40% by mass), respectively. The isoelectric point of the leakage inhibiting agent of sample 1 was measured by the method described above and found to be 4.71.

<Measurement of Degree of Viscosity>

The degree of viscosity at 25° C. (unit: mPa·s) of each of the first solution and the various solutions for degree of viscosity measurement obtained from sample 1 to sample 4 described above was determined by using a rheometer (manufactured by Anton Paar Japan K.K.) according to the method described above. Results thereof are shown in Table 1. In Table 1, for example, the degree of viscosity at 25° C. of the solution for degree of viscosity measurement including 10% by mass of the leakage inhibiting agent of sample 1 is shown where the row of sample 1 overlaps the column of 10% by mass. That is, according to the present test, the degree of viscosity at 25° C. of the solution for degree of viscosity measurement including 10% by mass of the leakage inhibiting agent of sample 1 was "2.5 mPa·s."

TABLE 1

| Sample No. | Mw | Isoelectric point | Concentration (% by mass) | | | | | | | | | | |
| --- | --- | --- | --- | --- | --- | --- | --- | --- | --- | --- | --- | --- | --- |
| | | | 1 | 5 | 6 | 7 | 8 | 9 | 10 | 20 | 30 | 40 | 50 |
| Sample 1 | 4000 | 4.65 | 1.0 | 1.3 | — | — | — | — | 2.5 | 5.1 | 9.1 | 17.1 | — |
| Sample 2 | 650 | 4.02 | — | — | — | — | — | — | 1.3 | 2.6 | 5.4 | 8.7 | 14.1 |
| Sample 3 | 20000 | 4.84 | — | 3.1 | 4.1 | 6.1 | 8.9 | 13.3 | 17.5 | 330.6 | — | — | — |
| Sample 4 | 5900 | 4.71 | — | — | — | — | — | — | — | 5.6 | 11.0 | 20.8 | — | manufactured by Nitta Gelatin Inc.) by heat such that the weight average molecular weight was 650, and this was used as the leakage inhibiting agent of sample 2. Next, various solutions for degree of viscosity measurement including the first solution described above were obtained by dissolving the leakage inhibiting agent in PBS buffer in such a way as to have concentrations shown in Table 1 (10% by mass, 20% by mass, 30% by mass, 40% by mass, and 50% by mass), respectively. The isoelectric point of the leakage inhibiting agent of sample 2 was measured by the method described above and found to be 4.02.

(Sample 3)

A gelatin hydrolysate was obtained by hydrolyzing a pig-derived alkali-treated gelatin hydrolysate having an isoelectric point of pH 5 (trade name: "beMatrix gelatin LS-H," manufactured by Nitta Gelatin Inc.) by heat such that the weight average molecular weight was 20000, and this was used as the leakage inhibiting agent of sample 3. Next, various solutions for degree of viscosity measurement were obtained by dissolving the leakage inhibiting agent in PBS buffer heated to 50° C. in such a way as to have concentrations shown in Table 1 (5% by mass, 6% by mass, 7% by mass, 8% by mass, 9% by mass, 10% by mass, and 20% by mass). The isoelectric point of the leakage inhibiting agent of sample 3 was measured by the method described above and found to be 4.84.

(Sample 4)

A gelatin hydrolysate was obtained by hydrolyzing a pig-derived alkali-treated gelatin hydrolysate having an isoelectric point of pH 5 (trade name: "beMatrix gelatin LS-H,"

<Discussion>

According to Table 1, the degree of viscosity at 25° C. of the first solution in sample 1 and sample 2 was 20 mPa·s or less. On the other hand, the degree of viscosity at 25° C. of the first solution in sample 4 exceeded 20 mPa·s. For sample 3, the degree of viscosity at 25° C. of the solution for degree of viscosity measurement including 20% by mass of the leakage inhibiting agent far exceeded 20 mPa·s, and thus it was presumed that the degree of viscosity at 25° C. of the first solution naturally exceeded 20 mPa·s. In addition, the isoelectric points of sample 1 and sample 2 were lower than those of sample 3 and sample 4 and were 4.7 or less (4.65 or less).

[Second Test]

In order to evaluate whether or not each sample described below exhibits a leakage inhibiting effect as the local injection preparation, the following test was carried out. Sample 21 and sample 22 are Examples, and sample 23 and sample 2A are Comparative Examples.

<Preparation of Specimens to be Injected>

A commercially available chicken thigh (produced in Japan) was obtained, and this was incubated at 37° C. to prepare specimens to be injected.

<Preparation of Samples (Local Injection Preparations)>

(Sample 21)

The leakage inhibiting agent (weight average molecular weight of gelatin hydrolysate: 4000) of sample 1 prepared in the first test was dissolved in a water-based solvent (specifically, PBS buffer) in such a way as to have concentrations shown in Table 2 (1% by mass, 5% by mass, 10% by mass, 20% by mass, 30% by mass, and 40% by mass) to obtain local injection preparations (sample 21) including the leakage inhibiting agent at the various concentrations, respectively.

(Sample 22)

The leakage inhibiting agent (weight average molecular weight of gelatin hydrolysate: 650) of sample 2 prepared in the first test was dissolved in a water-based solvent (specifically, PBS buffer) in such a way as to have concentrations shown in Table 2 (10% by mass, 20% by mass, 30% by mass, 40% by mass, and 50% by mass) to obtain local injection preparations (sample 22) including the leakage inhibiting agent at the various concentrations, respectively.

(Sample 23)

The leakage inhibiting agent (weight average molecular weight of gelatin hydrolysate: 20000) of sample 3 prepared in the first test was dissolved in a water-based solvent (specifically, PBS buffer) in such a way as to have concentrations shown in Table 2 (5% by mass, 6% by mass, 7% by mass, 8% by mass, 9% by mass, and 10% by mass) to obtain dispersions, and these dispersions were heated to 50° C. for dissolution to obtain local injection preparations (sample 23) including the leakage inhibiting agent at the various concentrations, respectively.

(Sample 2A)

Glycerin (reagent special grade, manufactured by FUJIFILM Wako Pure Chemical Corporation) was dissolved in a water-based solvent (specifically, PBS buffer) in such a way as to have concentrations shown in Table 2 (10% by mass, 40% by mass, and 50% by mass) to obtain local injection preparations (sample 2A) including glycerin at the various concentrations, respectively.

<Leakage Inhibition Test>

Syringes (manufactured by Terumo Corporation) including an injection needle having an outer diameter of 27 G were filled with 1 mL of the various local injection preparations of sample 21 to sample 23 and sample 2A described above, respectively, and the syringes were applied to the specimens to be injected described above to inject 0.2 mL (corresponding to 0.2 g) of the local injection preparations into the specimens to be injected, respectively. Next, the syringes were removed from the specimens to be injected, and puncture sites of the specimens to be injected were each covered with a commercially available filter paper (manufactured by ADVANTEC) cut into 1 cm squares to cause the filter paper to absorb the local injection preparation that leaked from the puncture site.

Finally, the mass of the filter paper that absorbed the local injection preparation that leaked from the puncture site was measured, and the leakage rate of the local injection preparation that leaked from the puncture site (%, the mass of the local injection preparation that leaked from the puncture site/0.2 g×100) was calculated. In the present test, when the leakage rate was 9.0% or less, it was considered that the local injection preparation had inhibited leakage from the target site. Results thereof are shown in Table 2. In Table 2, for example, the leakage rate (%) of the local injection preparation including 10% by mass of the leakage inhibiting agent in sample 21 is shown where the row of sample 21 overlaps the column of 10% by mass. That is, according to the present test, the leakage rate (%) of the local injection preparation including 10% by mass of the leakage inhibiting agent in sample 21 was 7.0%.

TABLE 2

|  |  |  |  |  |  |  |  |  |  |  |  | (27G) |
|  |  | Concentration (% by mass) | | | | | | | | | | |
|  | Sample No. | 1 | 5 | 6 | 7 | 8 | 9 | 10 | 20 | 30 | 40 | 50 |
| Leakage | Sample 21 | 14.0 | 11.5 | — | — | — | — | 7.0 | 2.5 | 9.0 | 14.1 | — |
| rate (%) | Sample 22 | — | — | — | — | — | — | 14.0 | 11.0 | 4.5 | 5.0 | 20.0 |
|  | Sample 23 | — | 11.0 | 10.5 | 4.0 | 5.0 | 10.5 | 19.0 | — | — | — | — |
|  | Sample 2A | — | — | — | — | — | — | 14.0 | — | — | 9.0 | 4.0 |

<Discussion>

According to Table 2, for sample 21, the leakage rate was 9.0% or less in the local injection preparations including 10 to 30% by mass of the leakage inhibiting agent, and for sample 22, the leakage rate was 9.0% or less in the local injection preparations including 30 to 40% by mass of the leakage inhibiting agent, suggesting that these samples each have a good leakage inhibiting effect.

On the other hand, for sample 23, the leakage rate was 9.0% or less in the local injection preparations including 7 to 8% by mass of the leakage inhibiting agent, but the local injection preparations used the leakage inhibiting agent consisting of the gelatin hydrolysate having a weight average molecular weight of 20000 and thus need to be prepared by heating to 50° C. for solation. Because of this, it was considered that the implementation of the local injection preparation was impractical and thus inappropriate. For sample 2A, the leakage rate was 9.0% or less in the local injection preparations including 40 to 50% by mass of glycerin, but glycerin may have an adverse influence on the administration site due to high osmotic pressure and thus it was considered that the implementation of the local injection preparation was impractical and thus inappropriate.

[Third Test]

In order to evaluate whether or not each sample described below exhibits a leakage inhibiting effect as the local injection preparation, the following test was carried out. Sample 31 is an Example, and sample 3A is a Comparative Example.

<Preparation of Specimens to be Injected>

A commercially available chicken thigh (produced in Japan) was obtained, and this was incubated at 37° C. to prepare specimens to be injected.

<Preparation of Samples (Local Injection Preparations)>

(Sample 31)

The leakage inhibiting agent (weight average molecular weight of gelatin hydrolysate: 4000) of sample 1 prepared in the first test was dissolved in a water-based solvent (specifically, PBS buffer) in such a way as to have concentrations shown in Table 3 (1% by mass, 5% by mass, 10% by mass, 20% by mass, 30% by mass, and 40% by mass) to obtain local injection preparations (sample 31) including the leakage inhibiting agent at the various concentrations, respectively.

(Sample 3A)

Glycerin (reagent special grade, manufactured by FUJI-FILM Wako Pure Chemical Corporation) was dissolved in a water-based solvent (specifically, PBS buffer) in such a way as to have concentrations shown in Table 3 (10% by mass, 40% by mass, and 50% by mass) to obtain local injection preparations (sample 3A) including glycerin at the various concentrations, respectively.

<Leakage Inhibition Test>

Syringes (manufactured by Terumo Corporation) including an injection needle having an outer diameter of 23 G were filled with 1 mL of the various local injection preparations of sample 31 and sample 3A described above, respectively, and the syringes were applied to the specimens to be injected described above to inject 0.2 mL (corresponding to 0.2 g) of the local injection preparations into the specimens to be injected, respectively. Thereafter, in the same manner as in the second test, a commercially available filter paper (manufactured by ADVANTEC) cut into 1 cm squares was caused to absorb the local injection preparation that leaked from the puncture site, and the mass of the filter paper was measured to calculate the leakage rate (%) of the local injection preparation that leaked from the puncture site.

In the present test, when the leakage rate was 11.0% or less, it was considered that the local injection preparation had inhibited leakage from the target site. Results thereof are shown in Table 3. In Table 3, for example, the leakage rate (%) of the local injection preparation including 30% by mass of the leakage inhibiting agent in sample 31 is shown where the row of sample 31 overlaps the column of 30% by mass. That is, according to the present test, the leakage rate (%) of the local injection preparation including 30% by mass of the leakage inhibiting agent in sample 31 was 10.0%.

TABLE 3

| | | Concentration (% by mass) | | | | | (23G) | |
| | Sample No. | 1 | 5 | 10 | 20 | 30 | 40 | 50 |
|---|---|---|---|---|---|---|---|---|
| Leakage rate (%) | Sample 31 | 22.0 | 15.5 | 13.0 | 12.0 | 10.0 | 3.0 | — |
| | Sample 3A | — | — | 22.0 | — | — | 14.0 | 12.0 |

<Discussion>

According to Table 3, for sample 31, the leakage rate was 11.0% or less in the local injection preparations including 30 to 40% by mass of the leakage inhibiting agent, suggesting that this sample has a good leakage inhibition effect. On the other hand, for sample 3A, the leakage rate exceeded 11.0% in each of the various local injection preparations including glycerin at the predetermined concentrations, respectively.

[Fourth Test]

In order to evaluate whether or not sample 41 described below exhibits a leakage inhibiting effect as the local injection preparation, the following test was carried out. Sample 41 is an Example.

<Preparation of Specimens to be Injected>

A commercially available chicken thigh (produced in Japan) was obtained, and this was incubated at 37° C. to prepare specimens to be injected.

<Preparation of Sample (Local Injection Preparations)>

(Sample 41)

The leakage inhibiting agent (weight average molecular weight of gelatin hydrolysate: 4000) of sample 1 prepared in the first test was dissolved in a water-based solvent (specifically, PBS buffer) in such a way as to have concentrations shown in Table 4 (1% by mass, 5% by mass, 10% by mass, 20% by mass, 30% by mass, and 40% by mass) to obtain local injection preparations (sample 41) including the leakage inhibiting agent at the various concentrations, respectively.

<Leakage Inhibition Test>

Syringes (manufactured by Terumo Corporation) including an injection needle having an outer diameter of 25 G were filled with 1 mL of the local injection preparations of sample 41 described above, respectively, and the syringes were applied to the specimens to be injected described above to inject 0.2 mL (corresponding to 0.2 g) of the local injection preparations into the specimens to be injected, respectively. Thereafter, in the same manner as in the second test, a commercially available filter paper (manufactured by ADVANTEC) cut into 1 cm squares was caused to absorb the local injection preparation that leaked from the puncture site, and the mass of the filter paper was measured to calculate the leakage rate (%) of the local injection preparation that leaked from the puncture site.

In the present test, when the leakage rate was 8.0% or less, it was considered that the local injection preparation had inhibited leakage from the target site. Results thereof are shown in Table 4. In Table 4, for example, the leakage rate (%) of the local injection preparation including 30% by mass of the leakage inhibiting agent in sample 41 is shown where the row of sample 41 overlaps the column of 30% by mass. That is, according to the present test, the leakage rate (%) of the local injection preparation including 30% by mass of the leakage inhibiting agent in sample 41 was 3.9%.

TABLE 4

| Sample | Concentration (% by mass) | | | | | (25G) |
|---|---|---|---|---|---|---|
| No. | 1 | 5 | 10 | 20 | 30 | 40 |
| Leakage rate (%) Sample 41 | 16.1 | 14.3 | 11.6 | 7.0 | 3.9 | 7.2 |

<Discussion>

According to Table 4, for sample 41, the leakage rate was 8.0% or less in the local injection preparations including 20 to 40% by mass of the leakage inhibiting agent, suggesting that this sample has a good leakage inhibition effect.

[Fifth Test]

In order to evaluate whether or not sample 51 described below exhibits a leakage inhibiting effect as the local injection preparation, the following test was carried out. Sample 51 is an Example.

<Preparation of Specimens to be Injected>

A commercially available chicken thigh (produced in Japan) was obtained, and this was incubated at 37° C. to prepare specimens to be injected.

<Preparation of Sample (Local Injection Preparations)>

(Sample 51)

The leakage inhibiting agent (weight average molecular weight of gelatin hydrolysate: 4000) of sample 1 prepared in the first test was dissolved in a water-based solvent (specifically, PBS buffer) in such a way as to have concentrations shown in Table 5 (1% by mass, 3% by mass, 5% by mass, 7.5% by mass, 10% by mass, 15% by mass, and 20% by mass) to obtain local injection preparations (sample 51) including the leakage inhibiting agent at the various concentrations, respectively.

<Leakage Inhibition Test>

Syringes (manufactured by Nippon Genetics Co., Ltd.) including an injection needle having an outer diameter of 33 G were filled with 1 mL of the local injection preparations of sample 51 described above, respectively, and the syringes were applied to the specimens to be injected described above to inject 0.2 mL (corresponding to 0.2 g) of the local injection preparations into the specimens to be injected, respectively. Thereafter, in the same manner as in the second test, a commercially available filter paper (manufactured by ADVANTEC) cut into 1 cm squares was caused to absorb the local injection preparation that leaked from the puncture site, and the mass of the filter paper was measured to calculate the leakage rate (%) of the local injection preparation that leaked from the puncture site.

In the present test, when the leakage rate was 2.5% or less, it was considered that the local injection preparation had inhibited leakage from the target site. Results thereof are shown in Table 5. In Table 5, for example, the leakage rate (%) of the local injection preparation including 10% by mass of the leakage inhibiting agent in sample 51 is shown where the row of sample 51 overlaps the column of 10% by mass. That is, according to the present test, the leakage rate (%) of the local injection preparation including 10% by mass of the leakage inhibiting agent in sample 51 was 2.1%.

TABLE 5

| Sample | Concentration (% by mass) | | | | | | (33G) |
|---|---|---|---|---|---|---|---|
| No. | 1 | 3 | 5 | 7.5 | 10 | 15 | 20 |
| Leakage rate (%) Sample 51 | 5.0 | 4.1 | 3.6 | 2.2 | 2.1 | 4.4 | 5.2 |

<Discussion>

According to Table 5, for sample 51, the leakage rate was 2.5% or less in the local injection preparations including 7.5 to 10% by mass of the leakage inhibiting agent, suggesting that this sample has a good leakage inhibition effect.

[Sixth Test]

In order to evaluate whether or not sample 61 described below exhibits a leakage inhibiting effect as the local injection preparation, the following test was carried out. Sample 61 is an Example.

<Preparation of Specimens to be Injected>

A commercially available chicken thigh (produced in Japan) was obtained, and this was incubated at 37° C. to prepare specimens to be injected.

<Preparation of Sample (Local Injection Preparations)>

(Sample 61)

The leakage inhibiting agent (weight average molecular weight of gelatin hydrolysate: 4000) of sample 1 prepared in the first test was dissolved in a water-based solvent (specifically, PBS buffer) in such a way as to have concentrations shown in Table 6 (1% by mass, 3% by mass, 5% by mass, 7.5% by mass, and 10% by mass) to obtain local injection preparations (sample 61) including the leakage inhibiting agent at the various concentrations, respectively.

<Leakage Inhibition Test>

Syringes (manufactured by Nippon Genetics Co., Ltd.) including an injection needle having an outer diameter of 37 G were filled with 1 mL of the local injection preparations of sample 61 described above, respectively, and the syringes were applied to the specimens to be injected described above to inject 0.2 mL (corresponding to 0.2 g) of the local injection preparations into the specimens to be injected, respectively. Thereafter, in the same manner as in the second test, a commercially available filter paper (manufactured by ADVANTEC) cut into 1 cm squares was caused to absorb the local injection preparation that leaked from the puncture site, and the mass of the filter paper was measured to calculate the leakage rate (%) of the local injection preparation that leaked from the puncture site.

In the present test, when the leakage rate was 1.0% or less, it was considered that the local injection preparation had inhibited leakage from the target site. Results thereof are shown in Table 6. In Table 6, for example, the leakage rate (%) of the local injection preparation including 10% by mass of the leakage inhibiting agent in sample 61 is shown where the row of sample 61 overlaps the column of 10% by mass. That is, according to the present test, the leakage rate (%) of the local injection preparation including 10% by mass of the leakage inhibiting agent in sample 61 was 1.1%.

TABLE 6

| | Sample | Concentration (% by mass) | | | | (37G) |
|---|---|---|---|---|---|---|
| | No. | 1 | 3 | 5 | 7.5 | 10 |
| Leakage rate (%) | Sample 61 | 2.0 | 1.3 | 0.6 | 0.6 | 1.1 |

<Discussion>

According to Table 6, for sample 61, the leakage rate was 1.0% or less in the local injection preparations including 5.0 to 7.5% by mass of the leakage inhibiting agent, suggesting that this sample has a good leakage inhibition effect.

[Seventh Test]

In order to evaluate whether or not each sample described below exhibits good cell retention as the local injection preparation, the following test was carried out. Sample 71 is an Example, and sample 73 and sample 7A are Comparative Examples.

<Preparation of Active Ingredient (Cell Suspension)>

A normal human fibroblast (manufactured by Kurabo Industries Ltd.) was dispersed in PBS buffer in a plastic container such that the concentration was $5.0 \times 10^5$ cells/mL to prepare a cell suspension.

<Preparation of Samples (Local Injection Preparations)>

(Sample 71)

To the cell suspension in the plastic container, the leakage inhibiting agent (weight average molecular weight of gelatin hydrolysate: 4000) of sample 1 prepared in the first test was added such that the final concentration of sample 1 was 20% by mass, and the cell was uniformly dispersed in the plastic container to prepare a local injection preparation (sample 71) having a final concentration of the cell of $2.5 \times 10^5$ cells/mL.

(Sample 73)

To the cell suspension in the plastic container, the leakage inhibiting agent (weight average molecular weight of gelatin hydrolysate: 20000) of sample 3 prepared in the first test was added such that the final concentration of sample 3 was 8.0% by mass, the cell was uniformly dispersed in the plastic container, and heated to 50° C. to prepare a local injection preparation (sample 73) having a final concentration of the cell of $2.5 \times 10^5$ cells/mL.

(Sample 7A)

To the cell suspension in the plastic container, PBS buffer was further added, and the cell was uniformly dispersed in the plastic container to prepare a local injection preparation (sample 7A) having a final concentration of the cell of $2.5 \times 10^5$ cells/mL.

<Cell Retention Test>

The absorbance at a wavelength of 600 nm of the local injection preparations of sample 71, sample 73, and sample 7A described above was measured by using an absorption spectrometer (manufactured by Thermo Fisher Scientific Inc.). Specifically, the absorbance at a wavelength of 600 nm of each sample 0 minutes, 2 minutes, 4 minutes, 6 minutes, 8 minutes, and 10 minutes after preparation was investigated with the absorption spectrometer. For the local injection preparation of each sample, the absorbance measured 0 minutes after preparation was regarded as a cell retention rate of 100%, and the cell retention rate was calculated from the absorbance measured at each time point. Here, the cell retention rate refers to an index that represents how uniformly a cell is dispersed in the local injection preparation. The less uniformly the cell is dispersed in the local injection preparation because of cell precipitation or the like, the lower the absorbance. Therefore, the lower the absorbance, the lower the cell retention rate. Results thereof are shown in Table 7.

TABLE 7

| | Sample | Post-suspension time (min) | | | | | |
|---|---|---|---|---|---|---|---|
| | No. | 0 | 2 | 4 | 6 | 8 | 10 |
| Cell retention rate (%) | Sample 71 | 100 | 98 | 95 | 90 | 85 | 70 |
| | Sample 73 | 100 | 105 | 100 | 95 | 90 | 80 |
| | Sample 7A | 100 | 50 | 40 | 20 | 15 | 10 |

<Discussion>

According to Table 7, the cell retention rate is maintained better in sample 71 and sample 73 than in sample 7A, and thus it is suggested that sample 71 and sample 73 have excellent cell retention. Therefore, it is considered that the local injection preparations of sample 71 and sample 73 have excellent cell retention, and thus can efficiently deliver the cell, which is the active ingredient, to a target site. However, the local injection preparation of sample 73 used the leakage inhibiting agent consisting of the gelatin hydrolysate having a weight average molecular weight of 20000 and needs to be prepared by heating to 50° C. for solation, and thus it was considered that the implementation of the local injection preparation was impractical and thus inappropriate.

[Eighth Test]

In order to evaluate whether or not each sample described below exhibits good cell ejection as the local injection preparation, the following test was carried out. Sample 81 is an Example, and sample 83 and sample 8A are Comparative Examples.

<Preparation of Active Ingredient (Cell Suspension)>

A cell suspension was prepared in the same manner as in the seventh test above.

<Preparation of Samples (Local Injection Preparations)>

(Sample 81)

A local injection (sample 81) having a leakage inhibiting agent (weight average molecular weight of gelatin hydrolysate: 4000) concentration of 20% by mass was prepared in the same manner as in the local injection preparation of sample 71 prepared in the seventh test.

(Sample 83)

A local injection preparation (sample 83) having a leakage inhibiting agent (weight average molecular weight of gelatin hydrolysate: 20000) concentration of 8.0% by mass was prepared in the same manner as in the local injection preparation of sample 73 prepared in the seventh test.

(Sample 8A)

A local injection preparation (sample 8A) having the cell uniformly dispersed in a plastic container was prepared in the same manner as in the local injection preparation of sample 7A prepared in the seventh test.

<Cell Ejection Test>

A cell ejection test was carried out on sample 81, sample 83, and sample 8A above by using the following method. That is, 3 mL of the local injection preparations of sample 81, sample 83, and sample 8A described above were sucked by using syringes (manufactured by Terumo Corporation) including an injection needle having an outer diameter of 27 G, respectively, and the local injection preparations were ejected from the syringes into plastic containers, respectively, immediately after suction and 10 minutes after suction followed by standing. Subsequently, in the plastic containers accommodating the local injection preparations, respectively, the absorbance at a wavelength of 600 nm of each sample was investigated with the same absorption spectrometer as used in the seventh test. For each sample, the absorbance measured in the local injection preparation with which a plastic container was filled without suction using the syringes was regarded as a cell ejection rate of 100%, and the cell ejection rate was calculated from the absorbance measured in the plastic container of each sample. Here, the cell ejection rate means an index that represents the extent to which cells are ejected to the outside after appropriately passing through the injection needle. The less appropriately the cells pass through the injection needle and are ejected to the outside, the lower the density of the cells in the plastic container, and thus the lower the absorbance. Therefore, the lower the absorbance, the lower the cell ejection rate. Results thereof are shown in Table 8. In Table 8, a local injection preparation with which a plastic container was filled without suction using the syringes is shown as "Control."

TABLE 8

| | Sample No. | Control | Immediately after suction | 10 min after suction |
|---|---|---|---|---|
| Cell ejection rate (%) | Sample 81 | 100 | 96 | 94 |
| | Sample 83 | 100 | 98 | 96 |
| | Sample 8A | 100 | 80 | 60 |

<Discussion>

According to Table 8, the cell ejection rate is maintained better in sample 81 and sample 83 than in sample 8A, and thus it is suggested that sample 81 and sample 83 have excellent cell retention. Therefore, it is considered that the local injection preparations of sample 81 and sample 83 have excellent cell retention, and thus can efficiently deliver the cell, which is the active ingredient, to a target site. However, the local injection preparation of sample 83 used the leakage inhibiting agent consisting of the gelatin hydrolysate having a weight average molecular weight of 20000 and needs to be prepared by heating to 50° C. for solation, and thus it was considered that the implementation of the local injection preparation was impractical and may cause damage to the cell and thus was inappropriate.

[Ninth Test: Solubility Evaluation]

While stirring 9 g of PBS buffer in containers at 200 rpm with a magnetic stirrer (manufactured by AS ONE Corporation), 1 g of sample 1 to sample 3 prepared in the first test were added to the containers, respectively. Stirring was stopped 1, 2, and 3 minutes after adding each sample, and it was visually checked whether or not a precipitate was observed in the containers. As a result, it was confirmed that sample 1 was dissolved after 2 minutes and sample 2 was dissolved after 1 minute, whereas most of sample 3 remained as a precipitate even after 3 minutes. Therefore, samples 1 and 2 dissolve relatively easily in a water-based solvent even at room temperature, and thus are considered to be easy to blend into an injection preparation.

The embodiment and Examples of the present invention have been described above, and it is also planned from the beginning to appropriately combine the configurations of the embodiment and Examples described above.

The embodiment and Examples disclosed this time should be considered to be illustrative in all respects and non-limiting. The scope of the present invention is defined by the Claims, not by the above description, and is intended to include all modifications within the meaning and scope equivalent to the Claims.

The invention claimed is:

1. A leakage inhibiting agent for a local injection preparation, comprising a gelatin hydrolysate having a weight average molecular weight of 5000 or less, wherein a degree of viscosity at 25° C. of a first solution obtained by dissolving the gelatin hydrolysate in phosphate buffered saline and adjusting a concentration of the gelatin hydrolysate to 40% by mass is 20 mPa·s or less.

2. The leakage inhibiting agent according to claim 1, wherein the leakage inhibiting agent consists of the gelatin hydrolysate.

3. The leakage inhibiting agent according to claim 1, wherein the leakage inhibiting agent is for a local injection preparation with which a syringe including an injection needle having an outer diameter of 23 G or more and 37 G or less is filled.

4. The leakage inhibiting agent according to claim 1, wherein the leakage inhibiting agent is for a local injection preparation with which a syringe including an injection needle having an outer diameter of 23 G or more and 27 G or less is filled.

5. A local injection preparation comprising the leakage inhibiting agent according to claim 1.

6. The local injection preparation according to claim 5, wherein the local injection preparation comprises 5% by mass or more and 40% by mass or less of the leakage inhibiting agent, and a degree of viscosity at 25° C. of the local injection preparation is 2 mPa·s or more and 20 mPa·s or less.

7. The local injection preparation according to claim 5, wherein the local injection preparation comprises 5% by mass or more and 40% by mass or less of the leakage inhibiting agent, and a degree of viscosity at 25° C. of the local injection preparation is 2 mPa·s or more and 10 mPa·s or less.

8. The local injection preparation according to claim 5, wherein the local injection preparation comprises 5% by mass or more and 40% by mass or less of the leakage inhibiting agent, and a degree of viscosity at 25° C. of the local injection preparation is 8 mPa·s or more and 20 mPa·s or less.

9. A method for producing the local injection preparation according to claim 5, the method comprising:

preparing the leakage inhibiting agent, a water-based solvent, and an active ingredient; and obtaining the local injection preparation by mixing the leakage inhibiting agent and the active ingredient into the water-based solvent at 1° C. or more and 30° C. or less.

10. The method for producing the local injection preparation according to claim 9, wherein the obtaining the local injection preparation is any of obtaining the local injection preparation by mixing the leakage inhibiting agent into the water-based solvent to obtain a first injection precursor and then mixing the active ingredient into the first injection precursor, or obtaining the local injection preparation by mixing the active ingredient into the water-based solvent to obtain a second injection precursor and then mixing the leakage inhibiting agent into the second injection precursor, or obtaining the local injection preparation by simultaneously mixing the leakage inhibiting agent and the active ingredient into the water-based solvent.

\* \* \* \* \*

5